(12) United States Patent
Tan et al.

(10) Patent No.: US 11,561,212 B1
(45) Date of Patent: Jan. 24, 2023

(54) METHOD FOR DETERMINING NOX SENSOR DATA FALSIFICATION BASED ON REMOTE EMISSION MONITORING

(71) Applicant: TONGJI UNIVERSITY, Shanghai (CN)

(72) Inventors: Piqiang Tan, Shanghai (CN); Chaojie Yao, Shanghai (CN); Lishuang Duan, Shanghai (CN); Yingjie Chen, Shanghai (CN); Zhiyuan Hu, Shanghai (CN); Diming Lou, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 0 days.

(21) Appl. No.: 17/726,663

(22) Filed: Apr. 22, 2022

(30) Foreign Application Priority Data

Nov. 8, 2021 (CN) .......................... 202111313294.X

(51) Int. Cl.
*G01N 33/00* (2006.01)

(52) U.S. Cl.
CPC ..... *G01N 33/0037* (2013.01); *G01N 33/0062* (2013.01); *F01N 2560/026* (2013.01); *F01N 2900/10* (2013.01)

(58) Field of Classification Search
CPC ...... F01N 11/00; G01N 21/3504; G06F 17/18
See application file for complete search history.

(56) References Cited

U.S. PATENT DOCUMENTS

| 7,798,413 | B2 | 9/2010 | Bi et al. |
| 8,266,892 | B2 | 9/2012 | Zapf et al. |
| 8,875,491 | B2 | 11/2014 | Zapf et al. |
| 2005/0161512 | A1* | 7/2005 | Jones ................. H04N 1/32133 235/487 |

\* cited by examiner

*Primary Examiner* — Anthony Ayala Delgado
(74) *Attorney, Agent, or Firm* — True Shepherd LLC; Andrew C. Cheng

(57) ABSTRACT

A method for determining NOx sensor data falsification based on remote emission monitoring, includes the steps of: acquiring a plurality of vehicle data sets and urea level data of to-be-tested reference vehicles, wherein vehicle data include NOx sensor readings and corresponding engine data vectors; acquiring urea level data of reference vehicles; calculating standard urea consumption per kilometer; (2) acquiring an average distribution probability of the vehicle data of the to-be-tested vehicles through a probability distribution evaluation step; counting a total proportion of invalid or negative NOx sensor readings in the plurality of vehicle data sets; determining whether the data of the to-be-tested vehicles satisfy one or more falsification conditions; if so, determining that the data from the NOx sensors of the to-be-tested vehicles are falsified; otherwise, determining that the data from the NOx sensors of the to-be-tested vehicles are not falsified.

10 Claims, 1 Drawing Sheet

METHOD FOR DETERMINING NOX SENSOR DATA FALSIFICATION BASED ON REMOTE EMISSION MONITORING

CROSS-REFERENCE TO RELATED APPLICATIONS

This application claims priority to Chinese Patent Application No. 202111313294.X with a filing date of Nov. 8, 2021. The content of the aforementioned application, including any intervening amendments thereto, is incorporated herein by reference.

TECHNICAL FIELD

The present disclosure relates to the field of emission testing and monitoring, in particular to a method for determining NOx sensor data falsification based on remote emission monitoring.

BACKGROUND ART

With desired power performance and economy, diesel engines (diesels) have become one of the main power sources of commercial vehicles and off-road mobile machinery. However, diesel engines emit a lot of nitrogen oxides (NOx), particulate matters (PM), hydrocarbons (HC) and carbon monoxide (CO), which has caused great pollution to the atmospheric environment and posed a great threat to the health of residents.

In an engine bench test, test conditions and test qualifications are easy to control, and a desirable result repeatability can be achieved. However, it cannot reflect the emission characteristics of heavy vehicles while the heavy vehicles are running on a real road. In a portable emission measurement system (PEMS) test, the actual emission in a single-lane road can be accurately evaluated. However, the test cost is relatively high, and vehicles cannot be monitored in real time. By remote monitoring based on technologies such as on-board diagnostics (OBD), the running data of vehicles, diesel engines and exhaust aftertreatment systems can be acquired in real time, and fault codes are reported. Therefore, the remote monitoring based on OBD plays an important role in the supervision of emissions of diesel engines.

In the markets, there have been NOx sensors that only send data, that is, the NOx sensors only send data with low NOx emission to an electronic control unit (ECU), which provides an emission falsification function. As an OBD remote monitoring terminal is installed on a vehicle in use, a controller area network (CAN) bus data stream is requested or acquired through an OBD interface, and the OBD remote monitoring terminal will acquire this falsification data stream, thus uploading false NOx sensor data. On the other hand, NOx sensor data falsification can also be made by falsifying the terminal.

SUMMARY

The present disclosure aims to overcome the above defects of the prior art and provides a method for determining NOx sensor data falsification based on emission remote monitoring, which has the advantages of low calculation complexity, high accuracy and high stability.

The aim of the present disclosure may be achieved by the following technical solutions:

A method for determining NOx sensor data falsification based on remote emission monitoring includes the steps of:

acquiring a plurality of vehicle data sets of reference vehicles to form reference data sets, and preprocessing the data, where each vehicle data set includes NOx sensor readings and corresponding engine data vectors, and the engine data vectors includes a plurality of types of engine data;

discretizing the engine data vectors to obtain a plurality of hypercubes, screening the reliability of the hypercubes and the reference data sets, and recording the screened hypercubes as selected characteristic working condition domains;

discretizing the NOx sensor readings to obtain a plurality of sensor reading ranges, and counting the distribution probability of each of the sensor reading ranges in each of the selected characteristic working condition domains according to the reference data sets to form a probability distribution model;

acquiring a plurality of vehicle data sets of to-be-tested vehicles to form to-be-tested data sets;

determining the selected characteristic working condition domain to which the engine data vectors of each vehicle data set in the to-be-tested data set belongs and the sensor reading range to which the NOx sensor readings belong, obtaining the distribution probability of each vehicle data set according to the probability distribution model, and calculating an average distribution probability of all vehicle data in the to-be-tested data sets;

determining whether the data of the to-be-tested vehicle satisfy one or more falsification conditions, if so, determining that the data from NOx sensors of the to-be-tested vehicles are falsified, otherwise determining that the data from the NOx sensors of the to-be-tested vehicles are not falsified, where the falsification conditions include:

the average distribution probability exceeds a set probability range; and a proportion of data points with a distribution probability of 0 in vehicle data is higher than a point proportion threshold value.

According to the method for determining NOx sensor data falsification provided by the present disclosure, normal NOx sensor readings and engine data of the reference vehicles are screened to finally obtain the probability distribution of the sensor readings corresponding to the engine data in a specific range under a normal condition; and whether the NOx sensor readings of the to-be-tested vehicle are falsified or not is discriminated based on the probability distribution according to the NOx sensor readings and the engine data of the to-be-tested vehicle. In this way, falsification of NOx sensors under on-board diagnostics (OBD) remote monitoring is discriminated with a low calculation complexity, and the NOx sensor readings are easy to process based on big data. Meanwhile, the method for determining NOx sensor data falsification provided by the present disclosure, based on a big data processing technology, is suitable for discriminating any NOx sensor falsification way and may be improved with updating of big data, thus maintaining or even improving the discrimination accuracy during data acquisition of a remote monitoring platform.

Further, the method also includes:

acquiring urea level data of the reference vehicle, calculating standard urea consumption per kilometer, acquiring urea level data of the to-be-tested vehicle, and calculating average urea consumption per kilometer of the to-be-tested vehicle;

the falsification conditions further include:

the average urea consumption is lower than the standard urea consumption, and the difference between the two is greater than a set difference; and a discrimination process is assisted with the average urea consumption, thus lowering a missing inspection rate.

Further, the falsification conditions also include:

a proportion of total invalid or negative NOx sensor readings in the to-be-tested data set is larger than a set proportion; and the discrimination process is assisted with the proportion of abnormal NOx sensor readings, thus lowering the missing inspection rate.

Further, a process of screening the reliability of the hypercubes and the reference data sets includes:

conducting screening four times sequentially to delete unreliable hypercubes and reference data sets;

a first screening: screening the hypercubes to obtain to-be-determined characteristic working condition domains;

a second screening: deleting abnormal vehicle data in the reference data sets in the to-be-determined characteristic working condition domains;

a third screening: screening the to-be-determined characteristic working condition domains to obtain a selected characteristic working condition domain; and a fourth screening: screening the vehicle data in the reference data sets.

Further, there are a plurality of reference vehicles.

The method further includes: acquiring vehicle identification numbers (VINs) of the reference vehicles;

the first screening specifically includes:

counting a distribution frequency of the engine data vectors in each hypercube in the reference data sets, and deleting the hypercubes with a distribution frequency lower than $f_{min}$, wherein $f_{min}$ is between 1.5 N/n and 10 N/n; and N represents the number of the vehicle data sets contained in the reference data sets;

counting types of the VINs corresponding to the engine data vectors distributed in each hypercube, and deleting the hypercubes of which the types are less than set types; and deleting the hypercubes with a lower distribution frequency and less VIN types by the first screening.

Further, the second screening specifically includes:

determining whether the NOx sensor readings $y_k$ corresponding to the engine data vectors distributed in each to-be-determined characteristic working condition domain satisfy a first determination inequality or not, if so, deleting the vehicle data corresponding to $y_k$, otherwise retaining the vehicle data corresponding to $y_k$;

the first determination inequality is as follows:

$$\left(y_k - \text{mean}(y_i)\right)^2 - \sum_{i \neq k}(y_i - \text{mean}(y_i))^2/(m-1) >$$
$$tor \times \sum_{i \neq k}(y_i - \text{mean}(y_i))^2/(m-1)$$

wherein, tor represents tolerability; m represents the total number of NOx sensor readings in the reference data sets, $y_i$ represents the NOx sensor readings except $y_k$ in the reference data sets, and mean ($y_i$) represents an average value of $y_i$; and deleting the vehicle data far out of the reading ranges of other sensors through the second screening.

Further, new unreliable hypercubes will appear after the second screening. Therefore, the third screening, the same as the first screening, includes deleting the unreliable hypercubes.

Further, the fourth screening specifically includes:

setting the distribution frequency of the vehicle data of the reference vehicles in the selected characteristic working condition domain to be $A_0$ and the distribution frequency of the vehicle data of the reference vehicles in the to-be-determined characteristic working condition domain to be $A_1$; considering the vehicle data of this reference vehicle to be unreliable if $A_0$ and $A_1$ have a too large difference and accordingly determining whether a second determination inequality works or not; if so, deleting the vehicle data of this reference vehicle in the selected characteristic working condition domain; otherwise retaining the vehicle data of this reference vehicle in the selected characteristic working condition domain.

The second determination inequality is as follows:

$$(A_1 - A_0)/A_1 > tor_V$$

wherein, $tor_V$ represents a tolerance proportion.

Further, the engine data includes engine torque, engine speed, engine coolant temperature, and exhaust gas temperature.

Further, the data preprocessing process specifically includes:

deleting the vehicle data in which the NOx sensor readings are not positive or 0 in the reference data sets; and normalizing the vehicle data.

The data preprocessing process improves the discrimination accuracy.

Compared with the prior art, the present disclosure has the following beneficial effects:

(1) According to the present disclosure, the normal NOx sensor readings and engine data of the reference vehicles are screened to finally obtain the probability distribution of the sensor readings corresponding to the engine data in a specific range under a normal condition; and whether the NOx sensor readings of the to-be-tested vehicle are falsified or not is discriminated based on the probability distribution according to the NOx sensor readings and the engine data of the to-be-tested vehicle. In this way, falsification of NOx sensors under OBD remote monitoring is discriminated with a low calculation complexity, and the NOx sensor readings are easy to process based on big data.

(2) The method for determining NOx sensor data falsification provided by the present disclosure, based on a big data processing technology, is suitable for discriminating any NOx sensor falsification way and may be improved with updating of big data, thus maintaining or even improving the discrimination accuracy during data acquisition of a remote monitoring platform and achieving a high stability.

(3) The present disclosure lowers the missing inspection rate by assisting the discrimination process with the average urea consumption and the invalid or negative NOx sensor readings in the to-be-tested data sets.

(4) According to the present disclosure, four times of screening is sequentially carried out to delete unreliable hypercubes and reference data sets. The hypercubes with a low distribution frequency and less VINs are deleted through the first screening. The vehicle data far out of the reading ranges of other sensors are deleted through the second screening. After the second screening, new unreliable hypercubes will appear, therefore the third screening, the same as the first screening, includes deleting the unreliable hypercubes. In the fourth screening, the unreliable vehicle data of the reference vehicles in four selected characteristic working condition domains are screened, thus achieving a high reliability of the probability distribution model and improving the discrimination accuracy.

DETAILED DESCRIPTION OF THE EMBODIMENTS

Figure 1:
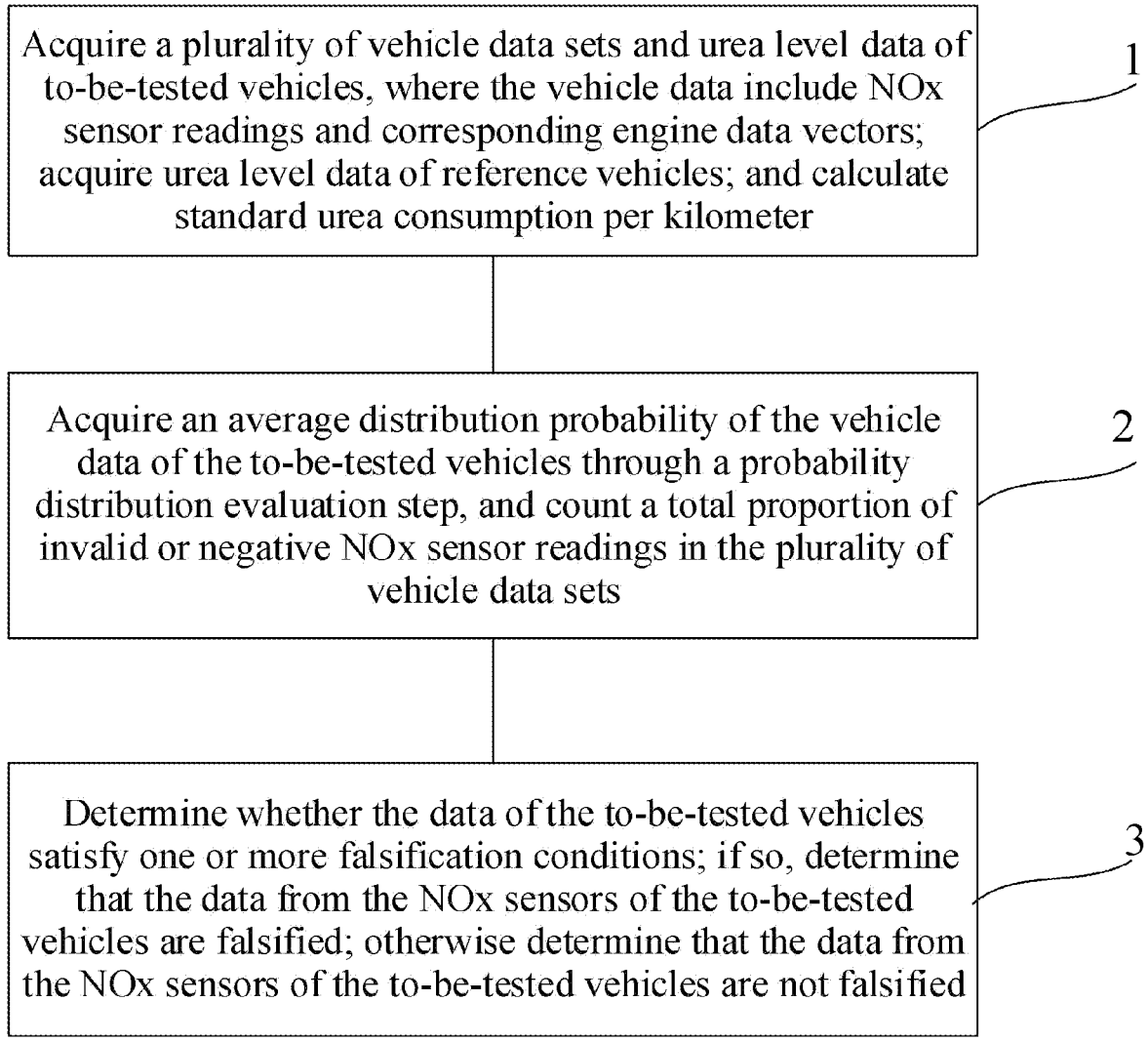
FIG. 1 is a schematic flowchart of the method of the present disclosure.

The present disclosure will be described in detail in conjunction with the accompanying drawings and specific embodiments. The embodiments are implemented on the premise of the technical solutions of the present disclosure. Detailed implementations and specific operation processes are provided. The protection scope of the present disclosure, however, is not limited to the following embodiments.

A method for determining NOx sensor data falsification based on remote emission monitoring, as shown in FIG. 1, includes the following steps:

(1) acquiring a plurality of vehicle data sets and urea level data of to-be-tested vehicles, where vehicle data include NOx sensor readings and corresponding engine data vectors; acquiring urea level data of reference vehicles; and calculating standard urea consumption per kilometer;

(2) acquiring average distribution probability of the vehicle data of the to-be-tested vehicles through a probability distribution evaluation step, and counting a proportion of total invalid or negative NOx sensor readings in the plurality of vehicle data sets;

(3) determining whether the data of the to-be-tested vehicles satisfy one or more falsification conditions, if so, determining that the data from NOx sensors of the to-be-tested vehicles are falsified, otherwise determining that the data from the NOx sensors of the to-be-tested vehicles are not falsified, where the falsification conditions include:

the average distribution probability exceeds a set probability range;

a proportion of data points with a distribution probability of 0 in vehicle data is higher than a point proportion threshold value;

the average urea consumption is lower than the standard urea consumption, and the difference of the two is larger than a set difference; and a proportion of total invalid or negative NOx sensor readings in the to-be-tested data sets is higher than 90%.

The plurality of vehicle data sets of the reference vehicles form reference data sets; and the engine data vectors include engine torque, engine speed, engine coolant temperature and exhaust gas temperature.

The probability distribution evaluation step in the step (2) includes the following sub-steps:

(21) preprocessing data of the reference data sets, including:

deleting the vehicle data in which the NOx sensor readings are not positive or 0 in the reference data sets; and normalizing the vehicle data;

(22) discretizing the engine data vectors to obtain a plurality of hypercubes, screening the reliability of the hypercubes and the reference data sets, and recording the screened hypercubes as selected characteristic working condition domains;

(23) discretizing the NOx sensor readings to obtain a plurality of sensor reading ranges, and counting the distribution probability of each sensor reading range in each selected characteristic working condition domain according to the reference data sets to form a probability distribution model;

(24) acquiring a plurality of vehicle data sets of to-be-tested vehicles to form to-be-tested data sets; determining the selected characteristic working condition domain to which the engine data vectors of each vehicle data set in the to-be-tested data set belongs and the sensor reading range to which the NOx sensor readings belong, obtaining the distribution probability of each vehicle data set according to the probability distribution model, and calculating an average distribution probability of all vehicle data in the to-be-tested data sets.

In the sub-step (21), the engine torque $d_{1-i}$, the engine speed $d_{2-i}$, the engine coolant temperature $d_{3-i}$ and the exhaust gas temperature $d_{4-i}$ are normalized through a first normalization formula as follows:

$$x^*_i = (x_i - \min(x))/(\max(x) - \min(x))$$

wherein $x_i$ and $x^*_i$ respectively represent the i-th data in to-be-normalized data sets before and after normalization; max(x) and min(x) respectively represent a maximum value and a minimum value in the to-be-normalized data sets; the normalized engine data vectors are expressed as follows:

$$(d_{1-i}^*, d_{2-i}^*, d_{3-i}^*, d_{4-i}^*)$$

The NOx sensor readings $y_i$ are normalized through a second normalization formula which is defined with reference to the SAE 1939 protocol:

$$y_i^* = (y_i - (-200))/(3012.75 - (-200))$$

wherein, $y_i^*$ represents a normalized NOx sensor reading.

In the sub-step (22), a process of discretizing the engine data vector includes:

carrying out data discretization on $(d_{1-i}^*, d_{2-i}^*, d_{3-i}^*, d_{4-i}^*)$, wherein a discretization range of each type of data is $int_j$ and set to be 0.01 to 0.1; and a discretization range table is as follows:

TABLE 1

| Discretization Range | |
|---|---|
| $j(d_j^*)$ | $int_j$ |
| 1 | 0.02 |
| 2 | 0.025 |
| 3 | 0.1 |
| 4 | 0.025 |

In the sub-step (23), the NOx sensor readings are discretized, and the discretization range $int_y$ is between 0.01 and 0.025.

In the sub-step (22), a process of screening the reliability of the hypercubes and the reference data sets includes:

conducting screening four times sequentially to delete unreliable hypercubes and reference data sets;

a first screening: screening the hypercubes to obtain to-be-determined characteristic working condition domains;

a second screening: deleting abnormal vehicle data in the reference data sets in the to-be-determined characteristic working condition domains;

a third screening: screening the to-be-determined characteristic working condition domains to obtain a selected characteristic working condition domain; and a fourth screening: screening the vehicle data in the reference data sets.

There are a plurality of reference vehicles.

The method further includes: acquiring VINs of the reference vehicles;

the first screening specifically includes:

counting a distribution frequency of the engine data vectors in each hypercube in the reference data sets, and deleting the hypercubes with a distribution frequency lower than $f_{min}$, where $f_{min}$ is between 1.5 N/n and 10 N/n; and N represents the number of the vehicle data sets contained in the reference data sets;

counting types of the VINs corresponding to the engine data vectors distributed in each hypercube, and deleting the hypercubes of which the types are less than set types; and deleting the hypercubes with a lower distribution frequency and less VIN types by the first screening.

The second screening specifically includes:

determining whether the NOx sensor readings $y_k$ corresponding to the engine data vectors distributed in each to-be-determined characteristic working condition domain satisfy a first determination inequality or not, if so, deleting the vehicle data corresponding to $y_k$, otherwise retaining the vehicle data corresponding to $y_k$;

the first determination inequality is as follows:

$$\left(y_k - \text{mean}(y_i)\right)^2 - \sum_{i \neq k}(y_i - \text{mean}(y_i))^2/(m-1) >$$
$$tor \times \sum_{i \neq k}(y_i - \text{mean}(y_i))^2/(m-1)$$

wherein tor represents tolerability and is 4 to 50; m represents the total number of NOx sensor readings in the reference data sets, $y_i$ represents the NOx sensor readings except $y_k$ in the reference data sets, and $\text{mean}(y_j)$ represents an average value of $y_i$; and deleting the vehicle data far out of the reading ranges of other sensors through the second screening.

New unreliable hypercubes will appear after the second screening. Therefore, the third screening, the same as the first screening, includes deleting the unreliable hypercubes.

The fourth screening specifically includes:

setting the distribution frequency of the vehicle data of the reference vehicles in the selected characteristic working condition domain to be $A_0$ and the distribution frequency of the vehicle data of the reference vehicles in the to-be-determined characteristic working condition domain to be $A_1$; considering the vehicle data of this reference vehicle to be unreliable if $A_0$ and $A_1$ have a too large difference and accordingly determining whether a second determination inequality works or not; if so, deleting the vehicle data of this reference vehicle in the selected characteristic working condition domain; otherwise retaining the vehicle data of this reference vehicle in the selected characteristic working condition domain.

The second determination inequality is as follows:

$$(A_1 - A_0)/A_1 > tor_V$$

wherein, $tor_V$ represents a tolerance proportion which is 0.01 to 0.5.

In the sub-step (23), the $(d_{1-i}^*, d_{2-i}^*, d_{3-i}^*, d_{4-i}^*)$ in the characteristic working condition domain is unnormalized as $(d_{1-i}^*, d_{2-i}^*, d_{3-i}^*, d_{4-i}^*)$. $y_i^*$ and a discretization range thereof are unnormalized as $y_j$; counting the distribution probability of each sensor reading range in each selected characteristic working condition domain according to the reference data sets to form a probability distribution model;

the probability distribution model f (y) is expressed as the following formula:

$$f(y) = P(|y_i - \text{mean}(y_i)| \geq |y - \text{mean}(y_i)|)$$

wherein, $\text{mean}(y_i)$ represents an average value of $y_i$; when $y - \text{mean}(y_i) = 0$, $f(y) = 1$; and when $|y - \text{mean}(y_i)|$ tends to be positive infinite or exceeds a certain limit, $f(y) = 0$.

The embodiment provides a method for determining NOx sensor data falsification based on remote emission monitoring, where normal NOx sensor readings and engine data of the reference vehicles are screened to finally obtain the probability distribution of the sensor readings corresponding to the engine data in a specific range under a normal condition; and whether the NOx sensor readings of the to-be-tested vehicle are falsified or not is discriminated based on the probability distribution according to the NOx sensor readings and the engine data of the to-be-tested vehicle. In this way, falsification of NOx sensors under OBD remote monitoring is discriminated with a low calculation complexity, and the NOx sensor readings are easy to process based on big data. Meanwhile, the method for determining NOx sensor data falsification provided by the present disclosure, based on a big data processing technology, is suitable for discriminating any NOx sensor falsification way and may be improved with updating of big data, thus maintaining or even improving the discrimination accuracy during data acquisition of a remote monitoring platform. The embodiment also lowers the missing inspection rate by assisting the discrimination process with the average urea consumption and the proportion of abnormal NOx sensor readings.

The foregoing is detailed description of the preferred specific embodiments of the present disclosure. It should be understood that a person of ordinary skill in the art can make various modifications and variations according to the concept of the present disclosure without creative efforts. Therefore, all technical solutions that a person skilled in the art can obtain based on the prior art through logical analysis, reasoning, or finite experiments according to the concept of the present disclosure shall fall within the protection scope defined by the appended claims.

What is claimed is:

1. A method for determining NOx sensor data falsification based on remote emission monitoring, comprising the steps of:

arranging a first sensor and at least a second sensor in association with each of reference vehicles, so that the first sensor and the at least one second sensor are operable to detect a plurality of vehicle data sets of reference vehicles to form reference data sets, and preprocessing the data, wherein each of vehicle data sets comprises NOx sensor readings detected by the first sensor and corresponding engine data vectors detected by the at least one second sensor, and the engine data vectors comprises a plurality of types of engine data;

discretizing the engine data vectors to obtain a plurality of hypercubes, screening the reliability of the hypercubes and the reference data sets, and recording the screened hypercubes as selected characteristic working condition domains;

discretizing the NOx sensor readings to obtain a plurality of sensor reading ranges, and counting the distribution probability of each of the sensor reading ranges in each of the selected characteristic working condition domains according to the reference data sets to form a probability distribution model;

arranging sensors in association with to-be-tested vehicles, so that the sensors detect a plurality of vehicle data sets of the to-be-tested vehicles to form to-be-tested data sets;

determining the selected characteristic working condition domain to which the engine data vectors of each of the vehicle data sets in the to-be-tested data set belongs and the sensor reading range to which the NOx sensor readings belong, obtaining the distribution probability of each vehicle data set according to the probability distribution model, and calculating an average distribution probability of all vehicle data in the to-be-tested data sets; and conducting a determination operation for determining whether the data of the to-be-tested vehicle satisfy one or more falsification conditions, and if so, determining that the data from NOx sensors of the sensors in association with the to-be-tested vehicles are falsified, otherwise determining that the data from the NOx sensors of the sensors in association with the to-be-tested vehicles are not falsified, wherein the to-be-tested data sets are collected in a remote monitoring platform and the determination operation is conducted in the remote monitoring platform, and wherein the falsification conditions comprise:

the average distribution probability exceeds a set probability range; and a proportion of data points with a distribution probability of 0 in vehicle data is higher than a point proportion threshold value.

2. The method according to claim 1, wherein the method further comprises:

arranging a first liquid level sensor in association with each of the reference vehicles, so that the first liquid level sensor detects urea level data of the reference vehicle, and a standard urea consumption per kilometer is determined for the reference vehicle, and arranging a second liquid level sensor in association with each of the to-be-tested vehicles so that the second liquid level sensor detects urea level data of the to-be-tested vehicle, and an average urea consumption per kilometer of the to-be-tested vehicle is determined, wherein the falsification conditions further comprise:

the average urea consumption is lower than the standard urea consumption, and the difference of the two is greater than a set difference.

3. The method according to claim 1, wherein the falsification conditions further comprise:

a proportion of total invalid or negative NOx sensor readings in the to-be-tested data sets is larger than a set proportion.

4. The method according to claim 1, wherein a process of screening the reliability of the hypercubes and the reference data sets comprises:

conducting screening four times sequentially;

a first screening: screening the hypercubes to obtain to-be-determined characteristic working condition domains;

a second screening: deleting abnormal vehicle data in the reference data sets in the to-be-determined characteristic working condition domains;

a third screening: screening the to-be-determined characteristic working condition domains to obtain a selected characteristic working condition domain; and a fourth screening: screening the vehicle data in the reference data sets.

5. The method according to claim 4, wherein there are a plurality of reference vehicles;

the method further comprises: acquiring vehicle identification numbers (VINs) of the reference vehicles;

the first screening specifically comprises:

counting a distribution frequency of the engine data vectors in each hypercube in the reference data sets, and deleting the hypercubes with a distribution frequency lower than $f_{min}$, where $f_{min}$ is between 1.5 N/n and 10 N/n; and N represents the number of the vehicle data sets contained in the reference data sets;

counting the VINs corresponding to the engine data vectors distributed in each hypercube; and deleting the hypercubes of which the VIN types are less than set types.

6. The method according to claim 5, wherein the second screening specifically comprises:

determining whether the NOx sensor readings $y_k$ corresponding to the engine data vectors distributed in each to-be-determined characteristic working condition domain satisfy a first determination inequality or not, if so, deleting the vehicle data corresponding to $y_k$, otherwise retaining the vehicle data corresponding to $y_k$;

the first determination inequality is as follows:

$$\left( y_k - \text{mean}(y_i) \right)^2 - \sum_{i \neq k} (y_i - \text{mean}(y_i))^2 / (m-1) > tor \times \sum_{i \neq k} (y_i - \text{mean}(y_i))^2 / (m-1)$$

wherein tor represents tolerability; m represents the total number of the NOx sensor readings in the reference data sets; $y_i$ represents the NOx sensor readings except $y_k$ in the reference data sets; and mean($y_i$) represents an average value of $y_i$.

7. The method according to claim 5, wherein the third screening is the same as the first screening.

8. The method according to claim 4, wherein the fourth screening specifically comprises:

setting the distribution frequency of the vehicle data of the reference vehicles in the selected characteristic working condition domain to be $A_0$ and the distribution frequency of the vehicle data of the reference vehicles in the to-be-determined characteristic working condition domain to be $A_1$;

determining whether a second determination inequality works or not; if so, deleting the vehicle data of this reference vehicle in the selected characteristic working condition domain; otherwise retaining the vehicle data of this reference vehicle in the selected characteristic working condition domain, wherein the second determination inequality is as follows:

$(A_1 - A_0)/A_1 > tor_V,$ wherein $tor_V$ represents a tolerance proportion.

9. The method according to claim 1, wherein the engine data comprise engine torque, engine speed, engine coolant temperature and exhaust gas temperature.

10. The method according to claim 1, wherein said preprocessing the data comprises:

deleting the vehicle data in which the NOx sensor readings are not positive or 0 in the reference data sets; and normalizing the vehicle data.

* * * * *